United States Patent
Chong

(10) Patent No.: US 10,426,336 B2
(45) Date of Patent: Oct. 1, 2019

(54) OPTICAL COHERENCE TOMOGRAPHY SYSTEM COMBINING TWO WAVELENGTHS

(71) Applicant: SANTEC CORPORATION, Komaki, Aichi (JP)

(72) Inventor: Changho Chong, Los Altos, CA (US)

(73) Assignee: SANTEC CORPORATION, Komaki (JP)

( * ) Notice: Subject to any disclaimer, the term of this patent is extended or adjusted under 35 U.S.C. 154(b) by 20 days.

(21) Appl. No.: 15/578,421

(22) PCT Filed: May 31, 2016

(86) PCT No.: PCT/US2016/035012
§ 371 (c)(1),
(2) Date: Nov. 30, 2017

(87) PCT Pub. No.: WO2016/196463
PCT Pub. Date: Dec. 8, 2016

(65) Prior Publication Data
US 2018/0206716 A1    Jul. 26, 2018

Related U.S. Application Data

(60) Provisional application No. 62/169,230, filed on Jun. 1, 2015.

(51) Int. Cl.
*A61B 3/10* (2006.01)
*G01N 15/14* (2006.01)
(Continued)

(52) U.S. Cl.
CPC .............. *A61B 3/102* (2013.01); *A61B 3/117* (2013.01); *A61B 3/12* (2013.01); *A61B 3/14* (2013.01);
(Continued)

(58) Field of Classification Search
CPC ........... A61B 3/102; A61B 3/10; A61B 3/117; A61B 3/12; A61B 3/14; G01B 9/02004;
(Continued)

(56) References Cited

U.S. PATENT DOCUMENTS

| 4,466,699 A | 8/1984 | Droessler et al. |
| 5,022,745 A | 6/1991 | Zayhowski et al. |

(Continued)

FOREIGN PATENT DOCUMENTS

| DE | 10 2011 114 797 A1 | 4/2013 |
| JP | 2006-202543 A | 8/2006 |

(Continued)

OTHER PUBLICATIONS

Changho Chong, et al. "Large Coherence Length Swept Source for Axial Length Measurement of the Eye." Applied Optics 48:10 (2009): D145-150.

(Continued)

*Primary Examiner* — William R Alexander
(74) *Attorney, Agent, or Firm* — Foley & Lardner LLP

(57) ABSTRACT

An optical coherence tomography (OCT) system combining multiple wavelengths is generally described. In an example, the OCT system includes a first light source configured to emit a first beam having a first wavelength. The OCT system further includes a second light source configured to emit a second beam having a second wavelength. The OCT system further includes an interferometer. The first beam and the second beam are configured to be directed into the interferometer. The interferometer includes a reference path and an interferometer sample path. The OCT system further includes a first beam splitter configured to divide, from an output of the interferometer sample path the first beam into a first sample path, and the second beam into a second sample path. The OCT system further includes a second (Continued)

beam splitter configured to combine the first beam and the second beam into a common axis.

20 Claims, 3 Drawing Sheets

(51) Int. Cl.
*A61B 3/117* (2006.01)
*A61B 3/12* (2006.01)
*A61B 3/14* (2006.01)
*G01B 9/02* (2006.01)

(52) U.S. Cl.
CPC ..... *G01B 9/02004* (2013.01); *G01B 9/02007* (2013.01); *G01B 9/02041* (2013.01); *G01B 9/02091* (2013.01); *G01N 15/1434* (2013.01); *G01N 2015/144* (2013.01); *G01N 2015/1454* (2013.01)

(58) Field of Classification Search
CPC ............ G01B 9/02007; G01B 9/02041; G01B 9/02091; G01N 15/1434; G01N 2015/144; G01N 2015/1454
See application file for complete search history.

(56) References Cited

U.S. PATENT DOCUMENTS

| | | | |
|---|---|---|---|
| 5,319,668 A | 6/1994 | Luecke | |
| 5,372,135 A | 12/1994 | Mendelson et al. | |
| 5,430,574 A | 7/1995 | Tehrani | |
| 5,537,162 A | 7/1996 | Hellmuth et al. | |
| 5,561,523 A | 10/1996 | Blomberg et al. | |
| 5,979,760 A | 11/1999 | Freyman et al. | |
| 5,982,963 A | 11/1999 | Feng et al. | |
| 6,070,093 A | 5/2000 | Oosta et al. | |
| 6,111,645 A | 8/2000 | Tearney et al. | |
| 6,134,003 A | 10/2000 | Tearney et al. | |
| 6,160,826 A | 12/2000 | Swanson et al. | |
| 6,275,718 B1 | 8/2001 | Lempert | |
| 6,282,011 B1 | 8/2001 | Tearney et al. | |
| 6,373,632 B1 | 4/2002 | Flanders | |
| 6,421,164 B2 | 7/2002 | Tearney et al. | |
| 6,485,413 B1 | 11/2002 | Boppart et al. | |
| 6,501,551 B1 | 12/2002 | Tearney et al. | |
| 6,556,853 B1 | 4/2003 | Cabib et al. | |
| 6,564,087 B1 | 5/2003 | Pitris et al. | |
| 6,725,073 B1 | 4/2004 | Motamedi et al. | |
| 7,099,358 B1 | 8/2006 | Chong | |
| 7,231,243 B2 | 6/2007 | Tearney et al. | |
| 7,323,680 B2 | 1/2008 | Chong | |
| 7,324,214 B2 | 1/2008 | De Groot et al. | |
| 7,352,783 B2 | 4/2008 | Chong | |
| 7,382,809 B2 | 6/2008 | Chong et al. | |
| 7,388,891 B2 | 6/2008 | Uehara et al. | |
| 7,400,410 B2 | 7/2008 | Baker et al. | |
| 7,414,779 B2 | 8/2008 | Huber et al. | |
| 7,428,057 B2 | 9/2008 | De Lega et al. | |
| 7,489,713 B2 | 2/2009 | Chong et al. | |
| 7,701,588 B2 | 4/2010 | Chong | |
| 7,725,169 B2 | 5/2010 | Boppart et al. | |
| 7,835,010 B2 | 11/2010 | Morosawa et al. | |
| 7,865,231 B2 | 1/2011 | Tearney et al. | |
| 7,869,057 B2 | 1/2011 | De Groot | |
| 7,884,945 B2 | 2/2011 | Srinivasan et al. | |
| 7,961,312 B2 | 6/2011 | Lipson et al. | |
| 8,036,727 B2 | 10/2011 | Schurman et al. | |
| 8,115,934 B2 | 2/2012 | Boppart et al. | |
| 8,315,282 B2 | 11/2012 | Huber et al. | |
| 8,405,834 B2 | 3/2013 | Srinivasan et al. | |
| 8,427,649 B2 | 4/2013 | Hays | |
| 8,500,279 B2 | 8/2013 | Everett et al. | |
| 8,625,104 B2 | 1/2014 | Izatt et al. | |
| 8,690,328 B1 | 4/2014 | Chong | |
| 8,690,330 B2 | 4/2014 | Hacker et al. | |
| 9,163,930 B2 | 10/2015 | Buckland et al. | |
| 9,335,154 B2* | 5/2016 | Wax | G01B 9/0209 |
| 9,851,433 B2 | 12/2017 | Sebastian | |
| 2002/0163948 A1 | 11/2002 | Yoshida et al. | |
| 2004/0036838 A1* | 2/2004 | Podoleanu | A61B 3/102 351/206 |
| 2005/0171438 A1 | 8/2005 | Chen et al. | |
| 2005/0201432 A1 | 9/2005 | Uehara et al. | |
| 2005/0213103 A1 | 9/2005 | Everett et al. | |
| 2006/0105209 A1 | 5/2006 | Thyroff et al. | |
| 2006/0109872 A1 | 5/2006 | Sanders | |
| 2006/0215713 A1 | 9/2006 | Flanders et al. | |
| 2007/0040033 A1 | 2/2007 | Rosenberg | |
| 2007/0076217 A1 | 4/2007 | Baker et al. | |
| 2007/0081166 A1 | 4/2007 | Brown et al. | |
| 2007/0133647 A1 | 6/2007 | Daiber | |
| 2007/0141418 A1 | 6/2007 | Ota et al. | |
| 2007/0263226 A1 | 11/2007 | Kurtz et al. | |
| 2007/0291277 A1 | 12/2007 | Everett et al. | |
| 2008/0097194 A1 | 4/2008 | Milner | |
| 2008/0269575 A1 | 10/2008 | Iddan | |
| 2009/0022181 A1 | 1/2009 | Atkins et al. | |
| 2009/0079993 A1* | 3/2009 | Yatagai | A61B 5/0062 356/497 |
| 2009/0103050 A1 | 4/2009 | Michaels et al. | |
| 2009/0169928 A1 | 7/2009 | Nishimura et al. | |
| 2009/0247853 A1 | 10/2009 | Debreczeny | |
| 2009/0268020 A1 | 10/2009 | Buckland et al. | |
| 2009/0290613 A1 | 11/2009 | Zheng et al. | |
| 2010/0110171 A1* | 5/2010 | Satake | A61B 3/102 348/78 |
| 2010/0157308 A1 | 6/2010 | Xie | |
| 2010/0246612 A1 | 9/2010 | Shimizu | |
| 2010/0253908 A1* | 10/2010 | Hammer | A61F 9/008 351/206 |
| 2010/0284021 A1 | 11/2010 | Hacker | |
| 2011/0112385 A1 | 5/2011 | Aalders | |
| 2011/0228218 A1 | 9/2011 | Hauger et al. | |
| 2011/0235045 A1 | 9/2011 | Koerner | |
| 2011/0255054 A1 | 10/2011 | Hacker et al. | |
| 2011/0299034 A1 | 12/2011 | Walsh et al. | |
| 2012/0013849 A1* | 1/2012 | Podoleanu | A61B 3/1005 351/221 |
| 2012/0026466 A1 | 2/2012 | Zhou et al. | |
| 2012/0133950 A1* | 5/2012 | Suehira | A61B 3/102 356/479 |
| 2012/0136259 A1 | 5/2012 | Milner et al. | |
| 2012/0188555 A1 | 7/2012 | Izatt et al. | |
| 2013/0265545 A1 | 10/2013 | Buckland et al. | |
| 2014/0051952 A1 | 2/2014 | Reichgott et al. | |
| 2014/0111774 A1 | 4/2014 | Komine | |
| 2014/0228681 A1 | 8/2014 | Jia et al. | |
| 2014/0268163 A1 | 9/2014 | Milner et al. | |
| 2014/0293290 A1 | 10/2014 | Kulkarni | |
| 2014/0336479 A1 | 11/2014 | Ando | |
| 2015/0348287 A1 | 12/2015 | Yi et al. | |
| 2016/0178346 A1 | 6/2016 | Kulkarni | |
| 2017/0090031 A1 | 3/2017 | Bondy et al. | |
| 2018/0088236 A1 | 3/2018 | Eichenholz et al. | |
| 2018/0128594 A1 | 5/2018 | Lee et al. | |

FOREIGN PATENT DOCUMENTS

| | | |
|---|---|---|
| JP | 2008-188047 | 8/2008 |
| JP | 2010-172538 | 8/2010 |
| WO | WO-2012/075126 A2 | 6/2012 |
| WO | WO-2013/168149 A1 | 11/2013 |
| WO | WO-2015/121756 A2 | 8/2015 |
| WO | WO-2017/176901 A1 | 10/2017 |

OTHER PUBLICATIONS

Chowdhury, Md Koushik et al., Challenges & Countermeasures in Optical Noninvasive Blood Glucose Detection, International Journal of Innovative Research in Science, Engineering and Technology vol. 2, Issue 1, Jan. 2013 (6 pages).

(56) References Cited

OTHER PUBLICATIONS

Dai et al., "Optical coherence tomography for whole eye segment imaging," Optics Express, vol. 20, No. 6 (2012) pp. 6109-6115.
Dhalla et al., "Simultaneous swept source optical coherence tomography of the anterior segment and retina using coherence revival," Optics Letters, vol. 37 No. 11, Jun. 1, 2012, pp. 1883-1885.
English Translation of the International Search Report and Written Opinion on International Application No. PCT/EP2009/009189, dated Apr. 6, 2010, 12 pages.
F. Lexer et al., "Wavelength-tuning interferometry of intraocular distances," Applied Optics, vol. 36, No. 25, pp. 6548-6553 (Sep. 1, 1997).
Fainman, Y. et al., "Nanophotonics for Information Systems," Information Optics and Photonics (T. Fournel and B. Javidi eds., Springer New York, 2010) pp. 13-37.
International Preliminary Report on Patentability and Written Opinion on International Application No. PCT/US2015/032726 dated Dec. 8, 2016(7 pages).
International Preliminary Report on Patentability in corresponding application PCT/US2016/035012 dated Dec. 14, 2017.
International Preliminary Report on Patentability in corresponding international application No. PCT/US2015/019299 dated Sep. 22, 2016.
International Preliminary Report on Patentability in corresponding international application No. PCT/US2015/032727 dated Dec. 8, 2016.
International Preliminary Report on Patentability in International appln. No. PCT/IB2015/000808.
International Search Report and Written Opinion dated Aug. 26, 2015 for PCT/US15/32727 (8 pages).
International Search Report and Written Opinion in corresponding application No. PCT/US2016/035012 dated Aug. 18, 2016.
International Search Report and Written Opinion in International Application No. PCT/US2015/19299 dated Nov. 2, 2015 (10 pages).
International Search Report and Written Opinion in PCT/IB2015/000808 dated Oct. 20, 2015 (12 pages).
Jeong et al., "Spectral-domain OCT with dual illumination and interlaced detection for simultaneous anterior segment and retina imaging," Optics Express, vol. 20, Issue 17, pp. 19148-19159 (2012).
Jia et al., Split-Spectrum Amplitude-Decorrelation Angiography with Optical Coherence Tomography, Optics Express, vol. 20 No. 4, Feb. 9, 2012, pp. 4710-4725.
Lexer et al., "Wavelength-tuning interferometry of intraocular distances", Applied Optics, vol. 36, No. 25, Sep. 1, 1997, pp. 6548-6553.
Mariampillai et al., Speckle Variance Detection of Microvasculature Using Swept-Source Optical Coherence Tomography, Optics Letters, vol. 33 No. 13, Jul. 1, 2008, pp. 1530-1532.
Nankivil et al.,"Handheld, rapidly switchable, anterior/posterior segment swept source optical coherence tomography probe," OSA Nov. 1, 2015; vol. 6, No. 11; DOI:10.1364/BOE.6.004516; Biomedical Optics Express 4516-4528.
Non-Final Rejection on U.S. Appl. No. 14/723,325 dated Dec. 7, 2017.
Notice of Allowance on U.S. Appl. No. 15/202,925 dated Feb. 13, 2018 (9 pages).
P. Tayebati et al., "Microelectromechanical tunable filter with stable half symmetric cavity," Electronics Letters, vol. 34, No. 20, pp. 1967-1968 (Oct. 1, 1998).
Poddar, et al., "Non-Invasive Glucose Monitoring Techniques: A Review and Current Trends," Oct. 31, 2008, pp. 1-47.
Sarlet, G. et al., "Wavelength and Mode Stabilization of Widely Tunable SG-DBR and SSG-DBR Lasers," IEEE Photonics Technology Letters, vol. 11, No. 11, Nov. 1999, pp. 1351-1353.
Segawa, Toru et al., "Semiconductor Double-Ring-Resonator-Coupled Tunable Laser for Wavelength Routing," IEEE Journal of Quantum Electronics, vol. 45, No. 7, Jul. 2009, pp. 892-899.
Sergie Ortiz, et al. "Corneal Topography From Spectral Optical Coherence Tomography (SOCT)." Biomedical Optics Express 2:12, (2011):3232-3247.
U.S. Notice of Allowance dated Dec. 6, 2013.
U.S. Notice of Allowance on U.S. Appl. No. 14/601,945 dated Sep. 13, 2016.
U.S. Notice of Allowance on U.S. Appl. No. 14/613,644 dated Nov. 7, 2016.
U.S. Notice of Allowance on U.S. Appl. No. 14/613,644 dated Nov. 18, 2016.
U.S. Notice of Allowance on U.S. Appl. No. 14/641,200 dated Jul. 12, 2016.
U.S. Office Action dated Sep. 12, 2013.
U.S. Office Action dated Aug. 19, 2015.
U.S. Office Action on U.S. Appl. No. 14/601,945 dated Mar. 2, 2016.
U.S. Office Action on U.S. Appl. No. 14/613,644 dated Jun. 8, 2016.
U.S. Office Action on U.S. Appl. No. 14/641,200 dated Mar. 14, 2016.
U.S. Office Action on U.S. Appl. No. 14/641,200 dated Dec. 7, 2015.
U.S. Office Action on U.S. Appl. No. 14/723,325 dated Nov. 18, 2016.
U.S. Office Action on U.S. Appl. No. 14/723,325 dated Apr. 24, 2017.
U.S. Office Action on U.S. Appl. No. 15/202,925 dated Jul. 27, 2017.
Chopra et al., Topographical Thickness of the Skin in the Human Face, Aesthetic Surgery Journal, vol. 35(8), 2015, pp. 1007-1013.
Final Office Action on U.S. Appl. No. 15/630,654 dated Sep. 12, 2018.
Non-Final Office Action on U.S. Appl. No. 14/723,325 dated Jan. 29, 2019.
Non-Final Office Action on U.S. Appl. No. 15/086,520 dated Aug. 6, 2018.
Non-Final Office Action on U.S. Appl. No. 15/611,515 dated Oct. 5, 2018.
Non-Final Office Action on U.S. Appl. No. 15/648,239 dated Jun. 6, 2018.
U.S. Office Action on U.S. Appl. No. 14/723,325 dated Apr. 19, 2019.
U.S. Office Action on U.S. Appl. No. 15/630,654 dated Apr. 4, 2018.
International Search Report and Written Opinion in PCT/US2019/027671 dated Jul. 1, 2019.

\* cited by examiner

OPTICAL COHERENCE TOMOGRAPHY SYSTEM COMBINING TWO WAVELENGTHS

CROSS-REFERENCE TO RELATED PATENT APPLICATIONS

This application is a U.S. national phase application under 35 U.S.C. § 371 of International Application No. PCT/US2016/035012, which claims priority to U.S. Provisional Application No. 62/169,230, filed Jun. 1, 2015, each of which is incorporated herein by reference in its entirety.

BACKGROUND

The following description is provided to assist the understanding of the reader. None of the information provided or references cited is admitted to be prior art.

Optical coherence tomography (OCT) is an imaging technique. OCT imaging techniques are often used in a medical setting. The techniques are capable of producing three dimensional images from within optical scattering samples, such as biological tissue. In other words, light scattered by a sample can be detected in order to form an image of the sample. When imaging a sample, parts of the sample below its surface can be imaged. Examples of biological tissue that may be imaged using OCT include coronary arteries, skin, and an eye. In another example, OCT may be used for art conservation to analyze layers of a painting.

OCT is often accomplished with the use of an interferometer. An interferometer utilizes light that is reflected back from a sample and a reference light. The reference light is generally configured to travel a similar distance as light that is reflected back from the sample. The light from the sample and the reference light can be combined in such a way that gives rise to an interference pattern. That is, the light from the sample and the reference light will either constructively or destructively interfere with each other. The level of interference that occurs indicates the reflectivity of areas of the sample, such that structures within the sample may be identified and imaged.

SUMMARY

In an embodiment, the present technology provides an improved optical coherence tomography (OCT) system combining two wavelengths capable, for example, of simultaneously imaging the anterior chamber and retina of an eye. In an illustrative embodiment, the OCT system includes a first light source configured to emit a first beam having a first wavelength. The OCT system further includes a second light source configured to emit a second beam having a second wavelength. The OCT system further includes an interferometer. The first beam and the second beam are configured to be directed into the interferometer. The interferometer includes a reference path and an interferometer sample path. The OCT system further includes a first beam splitter configured to divide, from an output of the interferometer sample path the first beam into a first sample path, and the second beam into a second sample path. The OCT system further includes a second beam splitter configured to combine the first beam and the second beam into a common axis.

An illustrative method includes emitting, by a first light source, a first beam having a first wavelength. The method also includes emitting, by a second light source, a second beam having a second wavelength. The method also includes directing the first beam and the second beam into an interferometer. The interferometer includes a reference path and an interferometer sample path. The method also includes dividing, by a first beam splitter from an output of the interferometer sample path the first beam into a first sample path, and the second beam into a second sample path. The method also includes combining, by a second beam splitter, the first beam and the second beam into a common axis.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION

Figure 1:
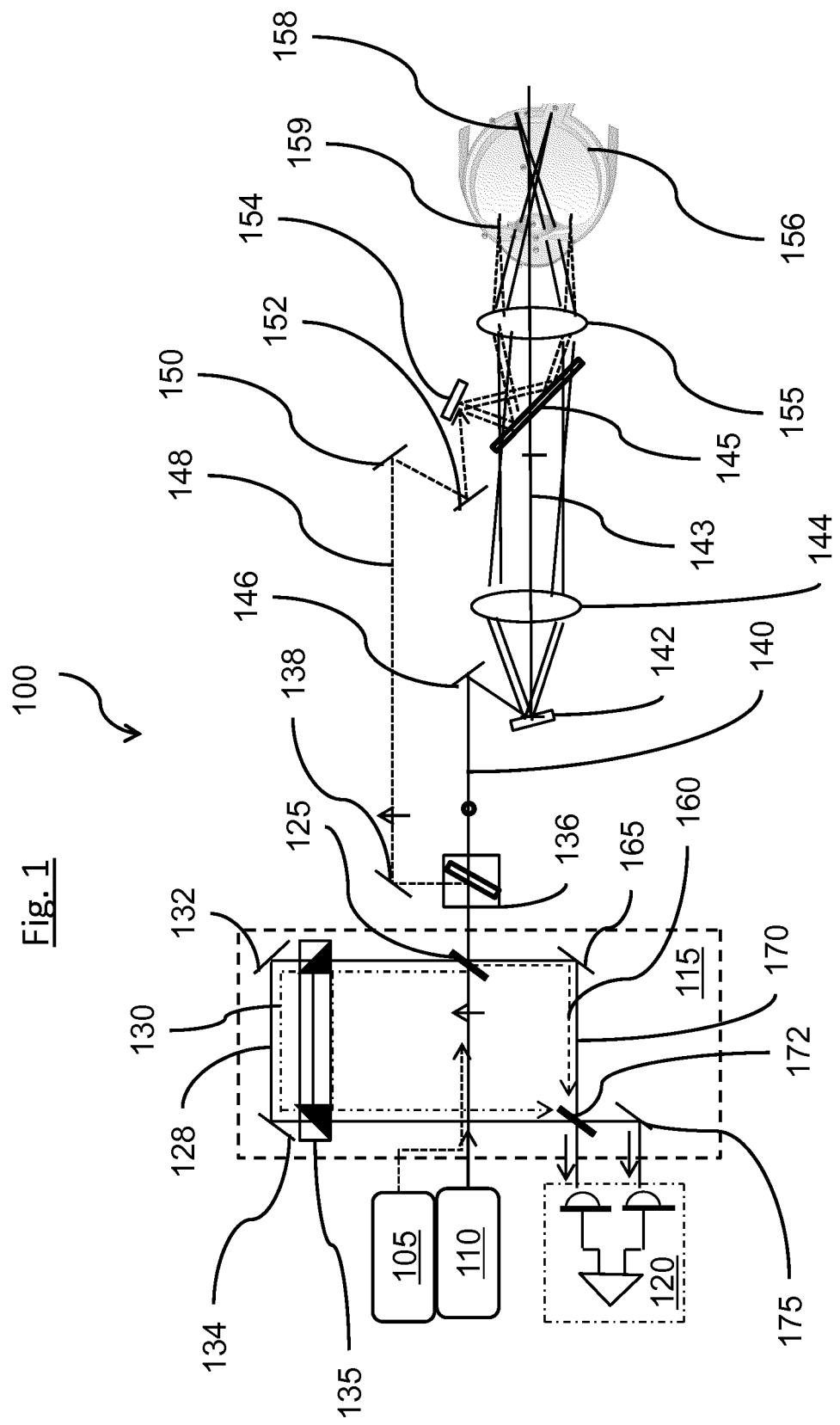
FIG. 1 depicts a representation of an optical coherence tomography (OCT) system combining two wavelengths in accordance with an illustrative embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

Described herein is an improved optical coherence tomography (OCT) system combining two wavelengths capable, for example, of simultaneously imaging the anterior chamber and retina of an eye.

Imaging the anterior chamber of an eye utilizes a different optical configuration than imaging for the retina of an eye. For the anterior chamber of the eye, a beam scan may be generally perpendicular to the sample (or cornea) and the beam has a shallow focus. When imaging the retina, a beam can be refracted by the eye itself, so a beam scan may be convergent with a collimated larger beam size for deep focusing in the eye. In other words, a beam used to scan the retinal area of the eye must enter the eye at a different angle than a beam used to scan the anterior chamber of the eye. Advantageously, the system and methods disclosed herein can image both the anterior chamber and the retina of an eye simultaneously by superimposing two light paths of different wavelength ranges suitable for eye imaging into one path. Such a configuration advantageously can reduce insertion loss of a combiner.

Further, the methods and systems disclosed herein can utilize a single detector and interferometer to detect two imaging ranges. Previously, systems have utilized multiple interferometers and multiple photo-detectors in order to image two samples at once. The methods and systems disclosed herein use a single interferometer and photo-detector, greatly decreasing the cost, complexity, and size of an OCT system designed to scan multiple samples at once.

The methods and systems disclosed herein advantageously also do not utilize complex mechanisms to adjust the focus and incidence angle of a single beam in order to realize multiple imaging ranges. Previously, systems may have used a single light source for scanning two different samples. However, such systems utilized complex switchable or adjustable lenses to adjust a single beam in order to switch between multiple imaging ranges. Such a configuration is complex, has many moving parts, and may be quite large. Further, such a configuration may not allow simultaneous and real time imaging of multiple imaging ranges. The methods and systems disclosed herein advantageously reduces the number of components utilized for multiple imaging ranges and allows for simultaneous and real time imaging of multiple imaging ranges. For example, the systems and methods disclosed herein can achieve real time imaging of two imaging ranges, such as an anterior chamber of an eye and the retinal area of an eye.

In an illustrative embodiment, two light sources are used to emit two beams with different wavelengths (or different bands of wavelength). In one embodiment, a wavelength swept source may be utilized to emit the two different beams. The output of the two light sources are combined into an interferometer. The interferometer includes a reference path and a sample path. The sample path is a path through which the beams are transmitted to be reflected off the sample (e.g., an eye). The reference path is a separate path through which the beams are reflected to have the same optical length as the sample path, such that the interferometer can generate an accurate image of the sample.

The sample path is output from the interferometer, and a first beam splitter splits the sample path into a first sample path and a second sample path. On a return path (when light from the sample paths is reflected or backscattered), the first beam splitter acts as a combiner, re-combining the first beam and the second beam into a common axis. In an embodiment, the first and second sample paths share a single common lens system, and the first beam in the first sample path is introduced into the middle of the common lens system. The first sample path is for a beam having (or band approximately around) a wavelength of 1,300 nanometers (nm). The second sample path is for a beam having (or band approximately around) a wavelength of 1,060 nanometers. In alternative embodiments, different wavelengths or bands of wavelengths may be used for the first and second beams (and subsequently the first and second sample paths).

The first and second sample paths are divided by a first dichroic mirror (the first beam splitter) at the root of the sample path of the interferometer. Such a dichroic mirror is specially configured to have transmission characteristics that reflect or transmit the light of the first beam and let the light of the second beam pass through (see discussion of FIG. 2 below).

The second sample path is configured with a scan mirror positioned at a focal point of a first lens of the common two lens system. The two lens system, in this embodiment, is in a 4f configuration. In alternative embodiments, the lens system may have more or less than two lenses, and may be in other configurations that the 4f configuration.

The second beam passes through the second lens resulting in a collimated beam configured for convergent scanning such that the second beam can scan the retinal area of the eye. In other words, the second sample path has a lens system with a collimating beam and a convergent scanning pattern relative to the sample. The collimating beam is focused at the retinal area after passing through the eye lens system and can be scanned across the retinal area because of convergent scanning before entering the eye. Accordingly, the path length of the second beam that scans the retinal area will be longer than the path length of the first beam that scans the anterior chamber of the eye. The difference between the first sample path length and the second sample path length can be an optical length equivalent to the axial length of a human eye. The second path also includes a second scan mirror for imaging the retinal area. The second scan mirror is located at the focal point of the first lens of the two lens system.

Light from the first beam that passes through the first sample path is introduced into the second lens of the two lens system by having a second beam splitter (here a dichroic mirror) positioned between the second lens and a focal point of the first lens. Here, the second beam splitter acts as a combiner, combining the first and second beams onto the same common axis. The scan mirror for the first sample path is positioned at a focal point of the second lens on the reflected path from the second beam splitter. When the first and second beams are reflected or backscattered from the sample, the second beam splitter splits the first and second beams back into the first and second sample paths, respectively. The first sample path and the first beam are configured to focus the beam such that the beam scans perpendicular to the anterior chamber position of the eye. In other words, the first sample path has a lens system with a divergent beam and lateral scanning pattern that is perpendicular to the sample.

When imaging the anterior chamber and the retinal area of the eye, the swept light sources (first and second light sources) are simultaneously and alternately modulated (see discussion below of FIG. 3). The backscattered reflected signals from the sample (here an eye) from the two different depth ranges (anterior chamber and retina) are reflected back along the same first and second sample paths to the single interferometer after being recombined by the two dichroic mirrors.

The detector can detect and analyze the received signals alternately for different time slots based on the two different wavelengths (or wavelength bands) of the first beam and the second beam. In other words, the detector can detect each of the reflected first and second beams that correspond with the two different imaging ranges. A processor decomposes the two imaging ranges into two images by selecting specific time slots of the detected signal. The processor may also control when the two light sources are swept so that the processor knows the specific time slots of the detected signal for each imaging range. In other words, the processor will recognize the first imaging range when the first beam is emitted to image the sample, and the processor will recognize the second imaging range when the second beam is emitted to image the sample.

Accordingly, the two wavelength ranges can provide anterior chamber and retinal area imaging of an eye simultaneously by superimposing two light paths into one, minimizing insertion loss of a combiner. Further, the system utilizes one single set of a detector and an interferometer that can be shared for both imaging ranges. This advantageously allows for a compact system that provides real time imaging of both the anterior chamber and retinal area of the eye.

FIG. 1 depicts a representation of an optical coherence tomography (OCT) system 100 combining two wavelengths in accordance with an illustrative embodiment. In alternative embodiments, fewer, additional, and/or different elements may be present. The OCT system includes a first light source 105 and a second light source 110. The first light source 105 emits a first beam 148 having a first wavelength. In FIG. 1, the first beam 148 is shown with dashed lines to differentiate it from a second beam 140.

The second beam 140 is emitted by the second light source 110 and has a second wavelength. The first beam 148 and the second beam 140 are combined and directed into an interferometer 115. The interferometer includes a reference path 128 and an interferometer sample path 170. The reference path 128 is shown by an arrow 130. The first beam 148 and the second beam 140 from the first light source 105 and the second light source 110 pass through the interferometer 115 to a mirror 125. The mirror 125 here is a half-mirror that reflects some of the light that hits it, but not all light. Accordingly, some of the first beam 148 and the second beam 140 are reflected into the reference path 128. The reference path 128 includes two different paths that correspond with a first sample path length and a second sample path length. That is, the reference path 128 will change depending on which part of the sample is being imaged (and subsequently which sample path is being utilized).

Accordingly, when the first sample path is being utilized with the first beam 148 to measure an anterior segment of an eye 156, the reference path 128 is longer, and the light is reflected off of a mirror 132 and a mirror 134. When the second sample path is being utilized with the second beam 140 to measure a retinal area of the eye 156, a path length switch 135 is activated to shorten the reference path 128, which corresponds to the difference in path length between the first sample path and the second sample path. In an alternative embodiment, the reference path 128 (and the shortened reference path when the path length switch 135 is activated) may be variable in order to provide depth scanning of the eye 156. In an alternative embodiment, instead of having a path length switch 135, the difference in path length between a reference path for the first beam 148 and a reference path for the second beam 140 may be pre-adjusted or predetermined in order to have relative offset/non-offset of depth ranges between the anterior chamber and retinal areas of the eye.

When the first beam 148 or the second beam 140 are reflected back from the first sample, they are reflected by the mirror 125 into the interferometer sample path 170. The interferometer sample path 170 is indicated by an arrow 160. The light in the interferometer sample path is reflected by a mirror 165. At a mirror 172 (here a half-mirror), the light from the reference path 128 and the interferometer sample path 170 are combined and are received by a balanced photo-detector 120, from which two images of the sample can be generated.

The first beam 148 and the second beam 140 output from the interferometer 115 arrive at a beam splitter 136. The beam splitter 136 divides the first beam 148 into a first sample path and the second beam 140 into a second sample path. To do so, the beam splitter 136 reflects or transmits the wavelength band of the first beam 148 but does not reflect or transmit the wavelength band of the second beam 140 (see discussion of FIG. 2 below). On the return path, when the first beam 148 and the second beam 140 have been reflected or backscattered, the beam splitter 136 acts as a combiner.

Accordingly, the first beam 148 is reflected into a first sample path to mirrors 125, 150, and 152 subsequently. After reflecting off of the mirror 152, the first beam 148 is reflected off of a scan mirror 154. The scan mirror 154 is configured to be at a focal point of a lens 155. The scan mirror 154 is also configured to direct the first beam 148 onto a beam splitter 145, which in turn reflects or transmits the first beam 148 into the lens 155. The beam splitter 145 is configured to recombine the first beam 148 on a common axis 143 as the second beam 140, which will be discussed more below. The first sample path therefore causes the first beam 148 to be a divergent beam with a lateral scanning pattern perpendicular to the sample, such that an anterior chamber of the eye 156 may be imaged. Any light of the first beam 148 that is backscattered and/or reflected can return to the interferometer along the same first sample path until it is recombined with the second beam 140 at the beam splitter 136. Backscattered and/or reflected light is split at the beam splitter 145 on the return path.

After passing through the beam splitter 136, the second beam 140 passes through the second sample path. This includes being reflected off of a mirror 146 and onto a scan mirror 142, which is configured to be at a focal point of a lens 144. The lens 144 and the lens 155, in this embodiment, are configured to be in a 4f configuration. The second beam 140 passes through the lens 144 and passes through the beam splitter 145 (see FIG. 2 discussion below) without being reflected. In this way, the first beam 148 and the second beam 140 are combined onto the common axis 143 so that each beam may scan the same sample (here the eye 156).

The second beam 140 also passes through the lens 155 such that the second beam 140 is a collimating beam with a convergent scanning pattern to scan the retinal area of the sample. Any light from the second beam 140 that is reflected or backscattered passes back through the second sample path where it will be recombined with the first beam 148 at the beam splitter 136.

Figure 2:
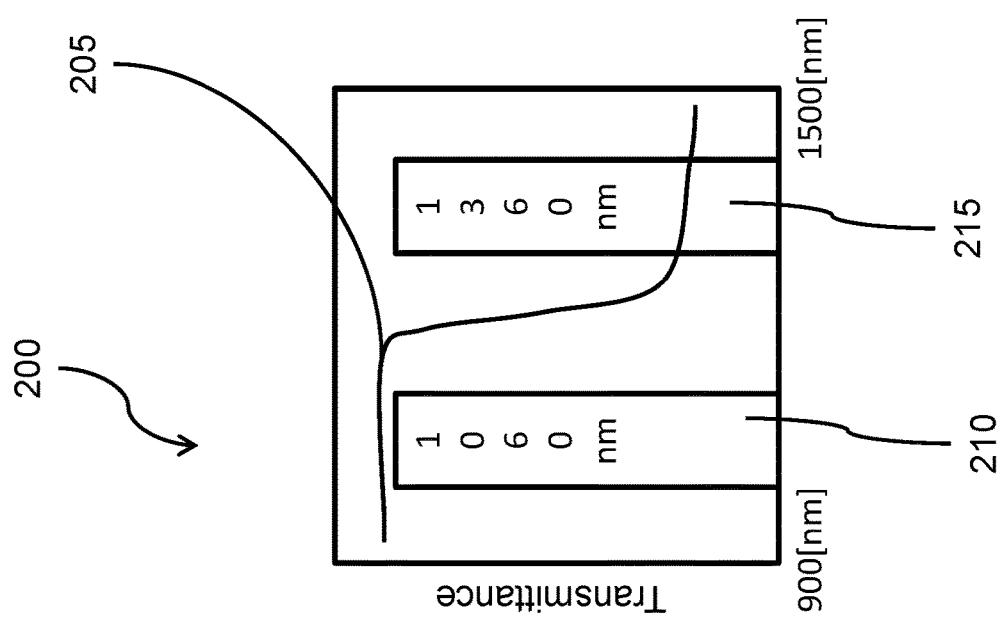
FIG. 2 depicts a graph that demonstrates properties of a dichroic mirror in an OCT system in accordance with an illustrative embodiment.

FIG. 2 depicts a graph 200 that demonstrates properties of a dichroic mirror in an OCT system in accordance with an illustrative embodiment. In alternative embodiments, fewer, additional, and/or different elements may be present. The graph 200 refers to an embodiment of a beam splitter that may be used in an illustrative embodiment. In particular, the beam splitter described in the graph 200 may be a dichroic mirror, and may be used as the beam splitter 136 and/or the beam splitter 145 as shown in FIG. 1 and discussed above.

The graph 200 has a first vertical axis related to transmittance. In other words, the higher the transmittance, the more light will pass through the beam splitter without being reflected. The horizontal axis is wavelength. Accordingly, the beam splitter has higher or lower transmittance depending on the wavelength of the light incident on the beam splitter. Here, the properties of a given beam splitter are shown by a line 205. For reference, a first wavelength band 210 and a second wavelength band 215 are also shown on the graph 200. Accordingly, light in the first wavelength band 210 (e.g., around 1,060 nanometers) is largely transmitted through the beam splitter, as demonstrated by FIG. 1 and discussed above. Conversely, light in the second wavelength band 215 (e.g., around 1,300 nanometers) is largely reflected by the beam splitter, as demonstrated by FIG. 1 and discussed above. As noted, in an embodiment, the beam splitter properties shown in FIG. 2 may be the beam splitter 136 and the beam splitter 145 shown in FIG. 1.

Figure 3:
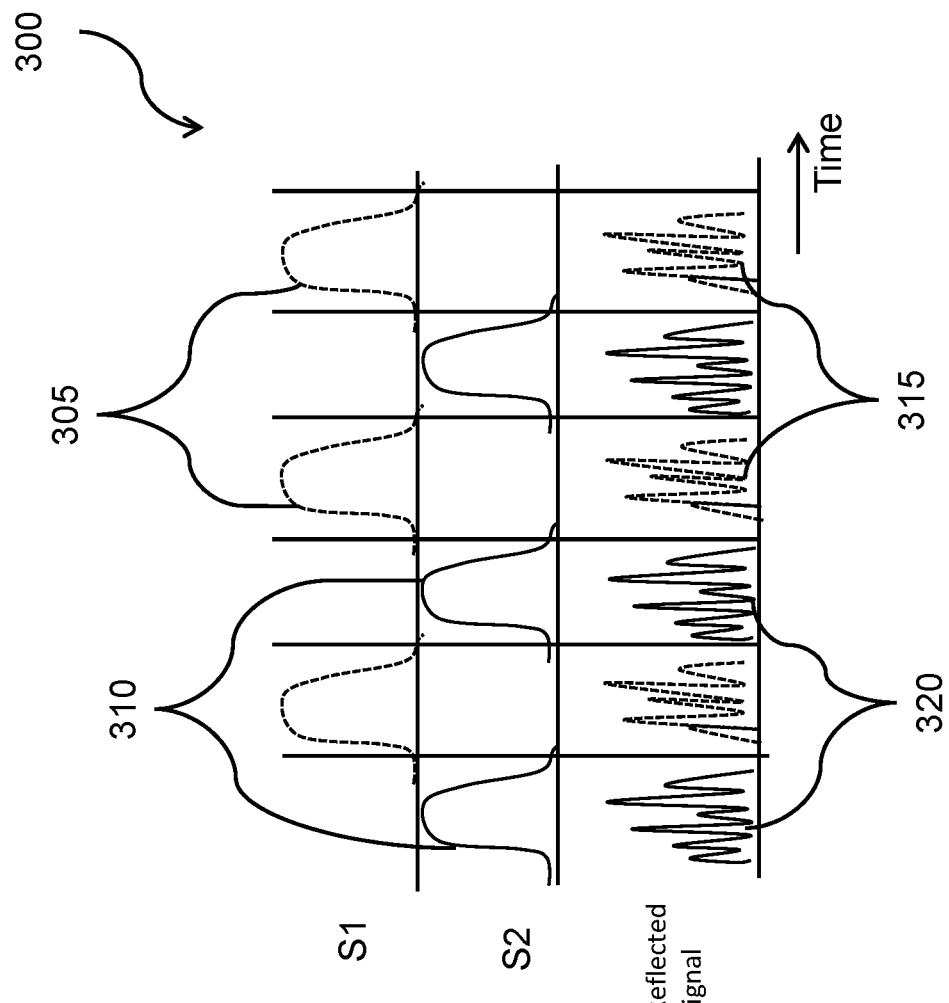
FIG. 3 depicts a graph that demonstrates how a first and second source are simultaneously and alternately modulated and detected in accordance with an illustrative embodiment.

FIG. 3 depicts a graph 300 that demonstrates how a first and second source are simultaneously and alternately modulated and detected in accordance with an illustrative embodiment. In alternative embodiments, fewer, additional, and/or different elements may be present. The graph 300 shows a first sample beam, for example beams 305. The graph 300 also shows a second sample beam, for example beams 310. The horizontal axis of the graph 300 is time. Accordingly, the graph 300 demonstrates how a system such as the one demonstrated in FIG. 1 may be controlled to turn on (or activate a swept source) of two different wavelengths (or wavelength bands) alternately at different times. Accordingly, the first beam and second beam are switched on and off in sequence.

The first beams 305 of the first sample may yield backscattered or reflected signals 315. The second beams 310 may yield backscattered or reflected signals 320. As an example, the reflected signals 315 may correspond to imaging of an anterior chamber via a first sample path as discussed above with respect to FIG. 1. Similarly, the reflected signals 320 may correspond to imaging of a retinal chamber via a second sample path as discussed above with respect to FIG. 1. The reflected signals 315 and the reflected signals 320 may both be received at a photo-detector, such as the photo-detector 120 shown in FIG. 1. In this way, a processing system in communication with the photo-detector can generate a first image and a second image based on the alternating received signals 315 and 320 received at the photo-receptor and output to the processing system. For example the two images may be of different image zones or depth ranges of a sample. If the path length difference of the first and second beams is pre-adjusted or predetermined and the signals from first and second beams are switched quickly, the system can generate simultaneous and real time images of both samples, in one embodiment the anterior chamber and retinal area of the eye 156.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. An optical coherence tomography (OCT) system comprising:
    a first light source configured to emit a first beam having a first wavelength;
    a second light source configured to emit a second beam having a second wavelength;
    an interferometer wherein the first beam and the second beam are configured to be directed into the interferometer, and further wherein the interferometer comprises:
      a reference path, and
      an interferometer sample path;
    a first beam splitter configured to divide, from an output of the interferometer sample path:
      the first beam into a first sample path, and
      the second beam into a second sample path; and
    a second beam splitter configured to combine the first beam and the second beam into a common axis.

2. The OCT system of claim 1, wherein:
    the first light source and the second light source are a wavelength swept source; and
    the first light source and the second light source are configured to be swept alternately.

3. The OCT system of claim 1, wherein:
    the first beam splitter comprises a dichroic mirror configured to reflect or transmit the first beam and not reflect or transmit the second beam; and the second beam splitter comprises a dichroic mirror configured to reflect or transmit the first beam and not reflect or transmit the second beam.

4. The OCT system of claim 1, wherein the first beam having the first wavelength is configured to image a different image zone or depth range of a sample than the second beam of the second wavelength.

5. The OCT system of claim 4, wherein the first beam is configured to image an anterior chamber of an eye and the second beam is configured image a retina of the eye.

6. The OCT system of claim 5, wherein the first wavelength is a band of approximately 1300 nanometers and the second wavelength is a band of approximately 1060 nanometers.

7. The OCT system of claim 4, wherein the first sample path has a divergent beam and a lateral scanning pattern perpendicular to the sample comprising:
 a first lens system, and
 a first scan mirror;
 wherein the second sample path has a collimating beam with a convergent scanning pattern, a second lens system, and a second scan mirror;
 wherein the second lens system comprises a first lens and a second lens configured in a 4f configuration, and the first lens system comprises the second lens; and
 wherein the first beam is introduced to the second lens through the first scan mirror positioned at a focal point of the second lens through the second beam splitter.

8. The OCT system of claim 1, wherein a path length difference between the first sample path and the second sample path is approximately an optical length equivalent to an axial length of a human eye.

9. The OCT system of claim 1, wherein:
 the interferometer comprises a reference path length switch configured to alternate a reference path length between a first reference length and a second reference length;
 the first reference length corresponds to a first sample path length; and
 the second reference length corresponds to a second sample path length.

10. The OCT system of claim 1, further comprising a photo-detector and a processing unit configured to:
 receive, through the photo-detector, the first beam and the second beam reflected from a sample; and
 generate a first image and a second image of the sample based on the first beam and the second beam.

11. A method comprising:
 emitting, by a first light source, a first beam having a first wavelength;
 emitting, by a second light source, a second beam having a second wavelength;
 directing the first beam and the second beam into an interferometer, wherein the interferometer comprises:
 a reference path, and
 an interferometer sample path;
 dividing, by a first beam splitter from an output of the interferometer sample path:
 the first beam into a first sample path, and
 the second beam into a second sample path; and
 combining, by a second beam splitter, the first beam and the second beam into a common axis.

12. The method of claim 11, wherein the first light source and the second light source are a wavelength swept source and wherein the method further comprises sweeping the first light source and the second light source alternately.

13. The method of claim 11, wherein:
 the first beam splitter comprises a dichroic mirror configured to reflect or transmit the first beam and not reflect or transmit the second beam; and
 the second beam splitter comprises a dichroic mirror configured to reflect or transmit the first beam and not reflect or transmit the second beam.

14. The method of claim 11, further comprising:
 imaging, from an output of a photo-detector, a first image zone or depth range of a sample with the first beam having the first wavelength; and
 imaging, from the output of the photo-detector, a second image zone or depth range of the sample with the second beam having the second wavelength.

15. The method of claim 14, wherein the first image zone or depth range of the sample is an anterior chamber of an eye and the second image zone or depth range of the sample is a retina of the eye.

16. The method of claim 15, wherein the first wavelength is a band of approximately 1300 nanometers and the second wavelength is a band of approximately 1060 nanometers.

17. The method of claim 14, wherein the first sample path has a divergent beam and a lateral scanning pattern perpendicular to the sample comprising:
 a first lens system, and
 a first scan mirror;
 wherein the second sample path has a collimating beam with a convergent scanning pattern, a second lens system, and a second scan mirror;
 wherein the second lens system comprises a first lens and a second lens configured in a 4f configuration, and the first lens system comprises the second lens; and
 the method further comprising introducing, through the second beam splitter, the first beam into the second lens through the first scan mirror positioned at a focal point of the second lens.

18. The method of claim 11, wherein a path length difference between the first sample path and the second sample path is approximately an optical length equivalent to an axial length of a human eye.

19. The method of claim 11, further comprising alternating, with a reference path length switch of the interferometer, a reference path length between a first reference length and a second reference length, wherein:
 the first reference length corresponds to a first sample path length, and
 the second reference length corresponds to a second sample path length.

20. The method of claim 11, further comprising:
 receiving, by a processing unit, through a photo-detector, the first beam and the second beam reflected from a sample; and
 generating, by the processing unit, a first image and a second image of the sample based on the first beam and the second beam.

* * * * *